United States Patent [19]
Katsoulis et al.

[11] Patent Number: 5,160,732
[45] Date of Patent: Nov. 3, 1992

[54] ENCAPSULATED ALUMINUM AND ALUMINUM-ZIRCONIUM COMPOSITIONS

[75] Inventors: Dimitris E. Katsoulis, Midland; Lori J. Conway, Hope; William J. Schulz, Jr., Midland, all of Mich.

[73] Assignee: Dow Corning Corporation, Midland, Mich.

[21] Appl. No.: 742,677

[22] Filed: Aug. 7, 1991

Related U.S. Application Data

[63] Continuation-in-part of Ser. No. 631,516, Dec. 21, 1990, abandoned.

[51] Int. Cl.$^5$ ............................................. A61K 7/38
[52] U.S. Cl. ........................................ 424/68; 424/66; 424/47; 424/401; 424/DIG. 5
[58] Field of Search ................ 424/47, DIG. 5, 68, 424/401, 66

[56] References Cited

U.S. PATENT DOCUMENTS

| | | | |
|---|---|---|---|
| 4,578,266 | 3/1986 | Tietjen et al. | 424/63 |
| 4,985,238 | 1/1991 | Tanner et al. | 424/66 |
| 5,017,360 | 5/1991 | Uatsoulis | 424/45 |
| 5,019,375 | 5/1991 | Tanner et al. | 424/66 |

Primary Examiner—Thurman K. Page
Assistant Examiner—Neil S. Levy
Attorney, Agent, or Firm—Sharon K. Severance

[57] ABSTRACT

Encapsulated aluminum and aluminum-zirconium salt compositions are produced by combining and heating an aqueous aluminum or aluminum-zirconium salt; a hydrophobic liquid; and a silicone carboxy acid or silicone carboxy acid derivative. The mixture is heated until substantially all of the free water has been removed. The encapsulated aluminum and aluminum-zirconium salt compositions precipitate out after the removal of the water. The encapsulated aluminum and aluminum-zirconium salt compositions are useful in deodorant and antiperspirant compositions.

26 Claims, No Drawings

ENCAPSULATED ALUMINUM AND
ALUMINUM-ZIRCONIUM COMPOSITIONS

This application is a continuation-in-part of application Ser. No. 07/631,516 filed on Dec. 21, 1990, now abandoned.

This invention pertains to encapsulated aluminum and aluminum-zirconium salt compositions. An aluminum or aluminum-zirconium salt is encapsulated in a shell comprising a silicone carboxy acid, silicone carboxy acid derivative or mixture thereof. The aluminum and aluminum-zirconium salts are released from the encapsulant in the presence of moisture and are useful in deodorant and antiperspirant compositions.

BACKGROUND OF THE INVENTION

It is known in the art to coat or encapsulate certain materials to provide a protective barrier to the material and/or to control the release characteristic of the material. A coated material is typically surrounded by a film wherein the film is "adhered" to the composition. An encapsulated material is typically surrounded by a film in the form of a shell or capsule wherein the shell or capsule is not necessarily adhered to the composition.

Topically applied materials such as cosmetics, lotions, fragrances, antiperspirants and deodorants, which contain ingredients that are encapsulated or coated, are known in the art. For example, Japanese Patent No. 86049285 teaches a transparent cosmetic composition comprising a fine powdered mica which is coated with a mixture of a hydrocarbon, a fatty acid, and a silicone oil and then baked at 100° C. to 150° C. for 1 for 5 hours. The coated mica gives a transparent appearance and soft brilliance to skin.

In antiperspirant or deodorant compositions, it is known to encapsulate or coat a deodorant active or a fragrance added to the deodorant or antiperspirant composition however, it is virtually unknown to encapsulate antiperspirant actives.

U.S. Pat. No. 4,803,195 to Holzner teaches a personal care composition having deodorant or antiperspirant activity comprising the deodorant or antiperspirant active and a perfume base wherein the perfume base is either in the form of an aqueous emulsion or in microencapsulated form. The perfume is released upon contact with moisture and can be re-encapsulated in situ.

U.S. Pat. No. 4,818,522 to Ferentchak et al. teaches antiperspirant compositions comprising water-immiscible adjuvants which are encapsulated in thick-walled, hollow, substantially spherical particles of an antiperspirant active. The water immiscible adjuvants include fragrances, antibacterials, antimicrobial or antifungal agents, deodorants or other dermatological preparations. The antiperspirant active are the encapsulant material and therefore Ferentchak et al. does not teach a method for encapsulating antiperspirant actives. The encapsulated water-immiscible adjuvants are prepared by emulsifying the adjuvant in an aqueous solution of the antiperspirant active and spray drying the resulting material.

EP Patent No. 0303461 to Wright teaches antiperspirant and deodorant compositions containing moisture sensitive capsules which in the presence of moisture release sensory agents such as perfumes, skin coolants, emollients, or other benefit agents such as deodorant actives, antiperspirant actives, and anticholinergic actives. The special polymer from which the capsules are formed is preferably a polysaccharide. The method for preparing the capsules comprises preparing an emulsion of water, the special polymer and the sensory or benefit agent and spray drying the emulsion. The only benefits obtained through the encapsulation of the antiperspirant active are believed to be the ability to produce stable alcoholic compositions and release of the agent in the presence of moisture.

U.S. Pat. No. 4,524,062 to Laba et al. teaches an antiperspirant/deodorant stick composition which comprises a powdered antiperspirant active, a coating material for the antiperspirant active, a deodorant and a cologne stick base. The coating material is typically a glycol stearate and the coated antiperspirant active is achieved by blending the antiperspirant active and the glycol stearate at a temperature at which the glycol stearate is a liquid. U.S. Pat. No. 4,524,062 does not teach a process for obtaining the antiperspirant active in an encapsulated form and there is no evidence to show that the antiperspirant active is even coated and not merely suspended in the glycol stearate.

It is an object of this invention to show encapsulated aluminum and aluminum-zirconium salt compositions.

It is further an object of this invention to show a method for producing the encapsulated aluminum and aluminum-zirconium salt compositions.

It is further an object of this invention to show a method for producing encapsulated aluminum and aluminum-zirconium salt compositions of a controlled particle size and shape.

It is further an object of this invention to show deodorant and antiperspirant compositions comprising the encapsulated aluminum and aluminum-zirconium salt compositions.

THE INVENTION

The encapsulated aluminum and aluminum-zirconium salt compositions (herein referred to as encapsulated salts) of this invention are comprised of aluminum or aluminum-zirconium salts contained in a shell comprised of a silicone carboxy acid or a silicone carboxy acid derivative. Upon contact with moisture, the shell opens up and releases the aluminum or aluminum-zirconium salt. Some or all of the aluminum or aluminum-zirconium salt may be dissolved in the moisture, depending on the concentration of the salt and moisture content.

The encapsulated salts of this invention are produced by combining together, with agitation, an aqueous aluminum salt or an aqueous aluminum-zirconium salt, a non-water miscible hydrophobic liquid (herein referred to as hydrophobic liquid), and a silicon carboxy acid or a silicone carboxy acid derivative (herein referred to as silicone carboxy) and heating the mixture to a temperature sufficient to remove substantially all of the free water. Some of the hydrophobic liquid may be removed during the heating because of an azeotrope that may form between the hydrophobic liquid and the water. It is important that the rate of water distillation be faster than the rate of hydrophobic liquid distillation. It is further preferred that any azeotrope formed contain more than 50% by weight of water. After the removal of the water, the encapsulated salts precipitate out of the reaction medium. Typically, an increase in the temperature will occur when the distillation of the aqueous phase is complete. Upon completion of the distillation there should be enough fluid remaining to keep the encapsulated composition free flowing. The encapsulated salts can then recovered through separation means such as filtration.

The aqueous aluminum salts and the aqueous aluminum-zirconium salts useful in the instant invention are those currently known in the art. The aluminum salts may be exemplified by aluminum nitrohydrate and aluminum halohydrates such as aluminum chlorohydrate, aluminum bromohydrate, and aluminum iodohydrate; and mixtures thereof. The aluminum salts useful in the instant invention may be further described as a standard (non-activated) or an activated salt. An activated salt, through compositional differences, is more efficacious when used in antiperspirant compositions.

The aluminum salts useful in the instant invention may be further described by the formula

$Al_a(OH)_bX_c$ where $\frac{1}{2} \geq a/c \geq 2.2/1$; c has the value of 0 to 5.9; $3a = b + c$; and X is selected from Cl, Br, I and $NO_3$.

The aluminum-zirconium salts may be exemplified by aluminum-zirconium halohydrates such as aluminum-zirconium chlorohydrate, aluminum-zirconium bromohydrate, and aluminum-zirconium iodohydrate and mixtures thereof. The aluminum-zirconium salts are typically buffered with an amino acid such as glycine. The aluminum-zirconium salts useful in the instant invention may be further described as a standard (non-activated or an activated salt. An activated salt, through compositional differences, is more efficacious when used in antiperspirant compositions.

The aluminum-zirconium salts useful in the instant invention may be further described by the formula

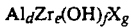
$Al_dZr_e(OH)_fX_g$ where d/e has the value of 0 to 20; f has the value of greater than 0; $3d + 4e = f + g$; and X is selected from Cl, Br, I and $NO_3$.

The aluminum and aluminum-zirconium salts are supplied as an aqueous solution containing greater than 0% by weight of the aluminum or aluminum-zirconium salt. The maximum amount of aluminum salt or aluminum-zirconium salt in the aqueous solution is dependent upon its solubility in water. Typically the aluminum salts are used as an aqueous solution comprising 10% to 50% by weight of the aluminum salt and typically the aluminum-zirconium salts are used as an aqueous solution comprising 10% to 40% by weight of the aluminum-zirconium salt. Aqueous solutions containing less than 10% by weight of the aluminum salt or aluminum-zirconium salt may be used to produce an encapsulated salt, however, they are not economically advantageous. Aqueous solutions containing greater than 50% by weight of the aluminum salt and greater than 40% by weight of the aluminum-zirconium salt are not well known in the art; however, they are useful when obtainable. The aqueous aluminum salts and aluminum-zirconium salts useful in the instant invention are commercially available or may be produced using methods known in the art.

Non-water miscible hydrophobic liquids useful in the instant invention may be selected from low viscosity silicone fluids, paraffin oils such as mineral oil, and mixtures thereof. The low viscosity silicones and further, low viscosity cyclic siloxanes are the preferred hydrophobic liquid.

Low viscosity silicones useful in the instant invention are selected from cyclic and linear silicones and mixtures thereof which have a viscosity of less than 1,000 centistokes. The cyclic low viscosity silicones may be exemplified by compounds having the formula

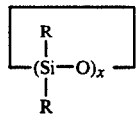

wherein each R is independently selected from an alkyl group containing 1 to 30 carbon atoms and an aryl group containing 6 to 10 carbon atoms and x has the value of 3 and 10. The preferred cyclic low viscosity silicone is when R is predominantly methyl and x is 4 to 5.

The cyclic low viscosity silicones may be further exemplified by, but not limited to hexamethylcyclotrisiloxane, octamethylcyclotetrasiloxane, decamethylcyclopentasiloxane, dodecamethylcyclohexasiloxane and mixtures thereof.

The linear low viscosity silicones may be exemplified by compounds having the formula

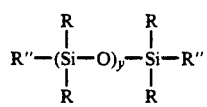

wherein each R is independently selected from an alkyl group containing 1 to 30 carbon atoms and an aryl group containing 6 to 10 carbon atoms; each R" is independently selected from R and a hydroxyl group; and y has the value such that the viscosity of the silicone is than 1,000 centistokes. The preferred linear low viscosity silicone is when R is predominantly methyl.

The linear low viscosity silicones may be further exemplified by, but not limited to, trimethylendblocked dimethylpolysiloxane fluids, 5, 10, 25 and 50 cS dimethylpolysiloxane fluids, hydroxyl endblocked polydimethylsiloxane fluids, octanmethyltrisiloxane, decamethyltetrasiloxane, and mixtures thereof.

The silicone carboxy acids and silicone carboxy acid derivatives useful in the instant invention may be exemplified by silicone carboxy acids, silicon carboxy acid derivatives or mixtures of thereof having the formula:

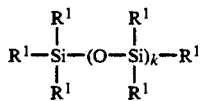

and

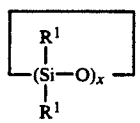

wherein each $R^1$ is independently selected from an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group, and a carboxy functional group having at least 2 carbon atoms, with the provision that at least one $R^1$ group is a carboxy functional group; k has the value of 1 to 1,000 and x has the value of 3 to 10.

$R^1$ may be a carboxy functional group wherein a carboxy functional group may be defined as a monovalent radical which contains a —COOH, —C(O)—O—C(O)—, —C(O)Cl, —C(O)O—Q, —C(O)O—W, or —C(O)SiR$^2$$_3$ radical, where Q is an alkali metal, W is glyceryl and $R^2$ is selected from an alkyl group containing 1 to 30 carbon atoms, an aryl group containing 6 to 10 carbon atoms, an alkaryl group containing 7 to 20 carbon atoms, and an aralkyl group containing 7 to 20 carbon atoms; and is attached to a silicon atom of the main molecular chain by a divalent linking group. Attachment to the silicon atom is through a silicon to carbon bond. The divalent linking group is an alkylene group containing at least 2 carbon atoms. There must be at least one carboxy functional group on the molecule. The carboxy functional group(s) may be located on the terminal ends of the polymer and/or along the polymer backbone.

The silicone carboxys useful in the instant invention include silicone carboxy acids, alkali metal silicone carboxylates, silicone acid chlorides, silicone acid anhydrides, glyceryl silicone carboxylates and mixtures thereof.

Specific silicone carboxy acids useful in the instant invention may be exemplified by, but not limited to

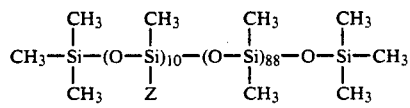

where Z may be —CH$_2$—CH(CH$_3$)COOH or —(CH$_2$)$_{10}$COOH;

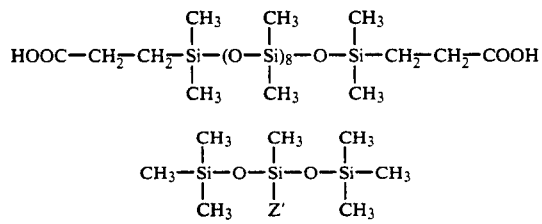

where Z' may be —CH$_2$—CH$_2$—CH$_2$COOH or —(CH$_2$)$_{10}$COOH;

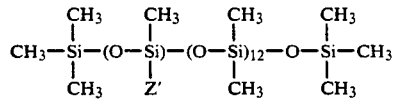

where Z' may be —CH$_2$—CH$_2$—CH$_2$COOH or —(CH$_2$)$_{10}$COOH;

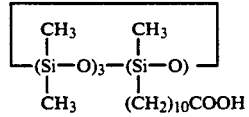

and others.

For the silicone carboxy to be useful in the instant invention it is necessary to the silicone carboxy to be soluble in the hydrophobic liquid and/or to have a melting point less than the water distillation temperature and further, the silicone carboxy must not be completely distillable at the water distillation temperature.

The encapsulated salts are formed by combining at least 14 millimoles of silicone carboxy for every 100 parts of aluminum or aluminum-zirconium salt (solids), and at least 1 part of hydrophobic liquid for every part of water. It is preferred to use between 20 to 200 millimoles of silicone carboxy per every 100 parts of aluminum or aluminum-zirconium salt and at least 1.25 part hydrophobic liquid per every part of water. It may be possible to use less than one part of hydrophobic liquid for every part of water if the amount of hydrophobic liquid lost in the distillation azeotrope is replaced during the course of the reaction.

The aqueous aluminum or aluminum-zirconium salts, silicone carboxy and hydrophobic liquid are combined and heated, with agitation, to a temperature sufficient to remove substantially all free water from the solution (water distillation temperature). Typically temperatures greater than 100° C., preferably 100° to 130° C., at atmospheric pressure, are useful for removing the free water. When the free water has been removed the temperature will rise above the water distillation temperature. It is preferred that the temperature does not exceed 150° C. for an extended period of time. Temperatures which exceed 150° C. for an extended period of time may be detrimental to the encapsulant and lead to fragmentation or cracking of the shell and possibly the conversion of the aluminum or aluminum-zirconium salt into an aluminum or aluminum-zirconium oxide. Pressures greater or less than atmospheric pressure can be employed in the method of the instant invention thereby allowing the mixture to be heated to higher or lower temperatures for the removal of the free water. It is essential that the water be removed during the heating step. Merely heating to temperatures greater than 100° C. while refluxing, or containing the water otherwise, will not result in an encapsulated salt. Typically, the completion of the water removal will be indicated by an increase in the temperature above the water distillation temperature.

After the removal of the free water from the mixture, the encapsulated salts precipitate out of the reaction medium. The encapsulated salts are typically recovered from the reaction medium by filtration means such as gravimetric, pressure or vacuum filters or by other separation means such as decanting or centrifuging. Filtration means will vary depending on the batch size. It is preferred to recover the encapsulated salts from the reaction medium at a temperature at or above the temperature at which the silicone carboxy is a liquid. It is further preferred to recover the encapsulated salts from the reaction medium using filtration means.

After the encapsulated salts have been recovered from the reaction medium, they may be optionally washed using a hydrophobic solvent to remove any excess silicone carboxy that might be adhered to the shells. If the silicone carboxy is not a liquid at room temperature it may be necessary to heat the hydrophobic solvent, during the wash, to a temperature at which the silicone carboxy is a liquid.

It is theorized that the shell material of the encapsulated salts is comprised of mostly silicone carboxy however, it may contain some hydrophobic liquid which may have been entrapped within the shell. Further, it is theorized that the shell comprises less than 5% and more then likely less than 1% of the total encapsulated salt mass. It is further theorized that the coating thickness is dependent upon the concentration of the silicone carboxy used. Typically the shells are spherical in nature however, they may also be elliptical, elongated or shaped otherwise. The standard aluminum and aluminum-zirconium salts do not appear to undergo a compositional change during the encapsulation process according to analysis based on High Performance Liquid Chromatography (HPLC).

The aluminum and aluminum-zirconium salts do not appear to be released from within the shell in any solvent or liquid except water or solvents containing water. In the presence of water the shells open up releasing the aluminum or aluminum-zirconium salt and some or all of the aluminum or aluminum-zirconium salt may be dissolved in the water depending on the amount of water present. Certain solvents such as paraffin oil, toluene, ethanol, hexane, propylene glycol, isopropyl myristate, and silicone glycol copolymers, did not appear to affect the shell or release the salts.

Another aspect of this invention is the ability to produce encapsulated aluminum and aluminum-zirconium salt compositions having a controlled particle size and shape. This aspect is accomplished by control of the concentration of the silicone carboxy and control of the agitation rate. The encapsulated aluminum and aluminum-zirconium salt compositions of this invention are produced using 14 or more millimoles silicone carboxy per every 100 parts aluminum or aluminum-zirconium salt. As the amount of silicone carboxy used increases, the beads formed become more spherical in shape and uniform in size.

Particle size distribution is controlled by the agitation rate (the rate of agitation during the water distillation). Encapsulated aluminum and aluminum-zirconium salt compositions which resemble impalpable powder (5 to 75 microns) can be produced at higher agitation rates. Because of equipment differences, mixing characteristics and other factors, it is not possible to specify an exact agitation rate that will produce an exact particle size however, one skilled in the art would be able to determine this.

The encapsulated salts of the instant invention are useful in deodorant and antiperspirant compositions such as aerosols, roll-ons, and sticks. It is preferable for the deodorant and antiperspirant compositions to be anhydrous, however, it is not necessary.

The aerosol compositions are typically comprised of 1 to 25% by weight of the encapsulated aluminum salt or 1 to 20% by weight of the encapsulated aluminum-zirconium salt; 50 to 90% by weight of a propellant, such as butane, isobutane, propane, nitrogen, carbon dioxide; and 5 to 15% by weight of an anhydrous carrier liquid. It is preferred that the aerosols comprise 8 to 12 wt. % of the encapsulated salt. Optional ingredients, such as cyclomethicone, dimethicone, isopropyl myristate, isopropyl palmitate, fragrance, deodorant, valve lubricants, talc, silica, suspending aids, polar activators, and others may be added into the aerosol compositions to improve the aesthetics or to change the characteristics of the propulsion. The aerosol compositions are produced using methods known in the art.

The roll-on compositions are typically comprised of 1 to 25% by weight of the encapsulated aluminum salt or 1 to 20% by weight of the encapsulated aluminum-zirconium salt; 60 to 95% by weight of a carrier liquid, such as water, cyclomethicone, organic esters and derivatives of organic esters, dioctyl adipate and others; and optionally 0.1 to 5% by weight of a suspending aid or 0.1 to 10% by weight of an emulsifier, such as glycerol monostearate, steareth-2, alkoxylates and others. If a suspending aid is used 0.1 to 2% of a polar activator must also be added. Preferably the roll-on compositions comprise 10 to 25 wt. % of the encapsulated salt. Other optional ingredients, such as fragrance, deodorants, talc, silica, polyethylene, silica, dimethicone, aluminum sulfate, starch, octenyl succinate and others, may be added into the roll-on compositions to improve the aesthetics or increase the viscosity of the composition. The roll-on compositions are produced using methods known in the art.

The stick compositions are typically comprised of 1 to 25% by weight of the encapsulated aluminum salt or 1 to 20% by weight of the encapsulated aluminum-zirconium salt; 20 to 65% by weight of a carrier fluid such as cyclomethicone, ethanol and propylene glycol; and 5 to 30% by weight of a gellant such as cetyl alcohol, stearyl alcohol, and hydrogenated aster oil. It is preferred that the stick compositions comprise 15 to 25 wt. % of the encapsulated salt. Optional ingredients, such as organic esters, organic ethers, emulsifiers, talc, silica, fragrance, deodorants, dimethicone, polyethylene and others, may be added to the stick compositions to improve the aesthetics or application of the active ingredient. The stick compositions are produced using methods known in the art.

Deodorant and antiperspirant compositions such as pump sprays, creams, lotions and others may also formulated with the encapsulated salts.

So that those skilled in the art can understand and appreciate the invention taught herein, the following examples are presented, it being understood that these examples should not be used to limit the scope of this invention over the limitation found in the claims attached hereto.

The term "parts" employed herein refers to parts by weight.

Particle Size Analysis: The particle size of the encapsulated salts was determined by using a Malvern 3600 EZ particle sizer. For analysis, the encapsulated salts were suspended in a solvent selected from either toluene or cyclomethicone and the stir speed was set at 4.

Physical Characteristics: The physical characteristics of the encapsulated salts (shape, cracks, jagged edges, etc.) was determined by observing the encapsulated salts under a 40× microscope.

Some of the encapsulated and unencapsulated aluminum and aluminum-zirconium salts were analyzed by HPLC according to the method taught in European Patent Application 0 256 831, herein incorporated by reference. Sample preparation for the encapsulated salts comprises weighing 1.0 grams of the encapsulated salt into a vial and adding 0.1N HCl to the vial until the total sample weight is 10 grams. The sample is shaken. 2 to 3 ml of the liquid are drawn off and filtered through a 0.45 micron syringe filter. The injected sample size is 2.0 microliters. In the instant application, Peak 4 corresponds with Band III, Peak 3 corresponds with Band II and Peak 2 corresponds with Band I as defined in European Patent Application 0 256 831.

EXAMPLE 1

25 grams of a mixture comprised of octamethylcyclotetra-siloxane and decamethylcyclopentasiloxane and 2.6 grams of a silicone carboxy acid having the structure

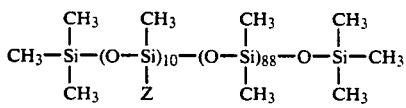

where Z is —CH$_2$—CH(CH$_3$)COOH were combined in a beaker and heated to 80° C. 12.5 grams of aqueous Aluminum Chlorohydrate (50% solids) was added to the silicone carboxy acid solution, with agitation. The mixture was heated maintaining a temperature around 110° C. while distilling off the water. The reaction was stopped when the temperature reached approximately 120° C. The mixture was then filtered through #1 Whatman filter paper to recover the encapsulated aluminum salt.

EXAMPLE 2

25 grams of a mixture comprised of octamethylcycloetetra-siloxane and decamethylcyclopentasiloxane and 2.52 grams of a silicone carboxy acid having the structure

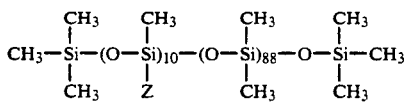

where Z is —CH$_2$—CH(CH$_3$)COOH were combined in a beaker with agitation. 12.6 grams of aqueous Aluminum-Zirconium Tetrachlorhydrex-Gly (35% solids) was added to the silicone carboxy acid solution, with agitation. The mixture was heated maintaining a temperature around 110° C. while distilling off the water. The reaction was stopped when it appeared that there was no more water coming off and the temperature started rising. The mixture was then filtered to recover the encapsulated aluminum-zirconium salt. The encapsulated salt was yellow in color and was a mixture of ellipsoids and spheres.

EXAMPLE 3

In a 125 ml beaker 12.5 grams of a mixture comprised of octamethylcyclotetrasiloxane and decamethylcyclopentasiloxane and 0.88 grams of a silicone carboxy acid of the formula

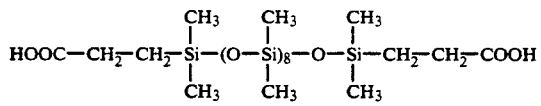

were combined and heated until the acid dissolved. 12.5 grams of aqueous aluminum-zirconium tetrachlorohydrex-gly (35% solids) was added and the mixture heated, with agitation, to boil off any water. Once all of the water boiled off the pot temperature started to rise (approximately 125° C.). Round, slightly yellow beads were left. The sample was vacuum filtered and air dried. An encapsulated aluminum-zirconium salt compound resulted.

EXAMPLE 4

In a 125 ml beaker 12.5 grams of a mixture comprised of octamethylcyclotetrasiloxane and decamethylcyclopentasiloxane and 0.44 grams of a silicone carboxy acid of the formula

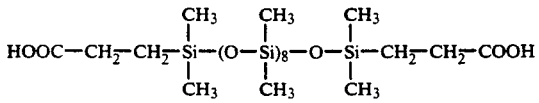

were combined and heated until the acid dissolved. 12.5 grams of aqueous aluminum chlorohydrate (50% solids) was added and the mixture heated to approximately 100° C., with agitation, to boil off any water. Once all of the water boiled off, material encapsulated to fine, off-white spheres. An encapsulated aluminum chlorohydrate salt compound resulted.

EXAMPLE 5

In a 125 ml beaker 12.5 grams of a mixture comprised of octamethylcycloetetrasiloxane and decamethylcyclpentasiloxane and 0.88 grams of a silicone carboxy acid of the formula

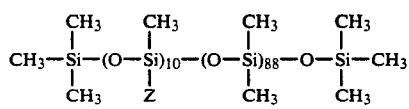

where Z is —(CH$_2$)$_{10}$COOH were combined and heated until the acid dissolved. 12.5 grams of aqueous aluminum-zirconium tetrachlorohydrex-gly (35% solids) was added and the mixture heated, with agitation to boil off any water. The water boiled off rapidly leaving behind small, slightly yellow encapsulated beads. The sample was vacuum filtered and air dried. An encapsulated aluminum-zirconium salt compound resulted.

EXAMPLE 6

In a 125 ml beaker 12.5 grams of a mixture comprised of octamethylcyclotetrasiloxane and decamethylcyclopentasiloxane and 1.25 grams of a silicone carboxy acid of the formula

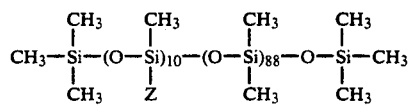

where Z is —(CH$_2$)$_{10}$COOH were combined and heated until the acid dissolved. 12.5 grams of aqueous aluminum chlorohydrate (50% solids) was added and the mixture heated, with agitation to boil off any water. The water boiled off rapidly leaving behind small, white encapsulated particles. The sample was vacuum filtered and air dried. An encapsulated aluminum chlorohydrate salt compound resulted.

EXAMPLE 7

150 grams cyclomethicone comprised mostly of octamethylcyclotetrasiloxane and decamethylcyclopentasiloxane and 29.19 grams of a silicone carboxy acid having the formula

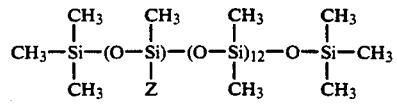

where Z is —(CH$_2$)$_3$COOH were combined in a 500 ml round bottom flask equipped with a paddle-blade agitator, a water cooled condenser and a 250 ml round bottom receiver. The mixture was heated to 73° C. 150 grams of aqueous aluminum-zirconium tetrachlorohydrex-gly (35% solids) was added to the silicone acid solution with agitation. The mixture was heated for approximately 3.5 hours, while distilling off the water, maintaining a temperature around 101° C. The reaction was stopped when the pot temperature reached approximately 118° C. The mixture was then vacuum filtered (while hot, −80° C.), using a Buchner funnel, to recover 49.9 grams of encapsulated aluminum-zirconium salt.

EXAMPLE 8

150 grams cyclomethicone comprised mostly of octamethylcyclotetrasiloxane and decamethylcyclopentasiloxane and 8.95 grams of a silicone carboxy acid having the formula

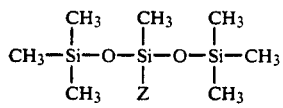

where Z is —(CH$_2$)$_{10}$COOH were combined in a 500 ml round bottom flask equipped with a paddle-blade agitator, a water cooled condenser and a 250 ml round bottom receiver. The mixture was heated to 80° C. 150 grams of aqueous aluminum-zirconium tetrachlorohydrex-gly (35% solids) was added to the silicone acid solution with agitation. The mixture was heated for approximately 3 hours, while distilling off the water, maintaining a temperature around 103° C. The reaction was stopped when the pot temperature reached approximately 127° C. The mixture was then vacuum filtered (while hot, ~80° C.), using a Buchner funnel, to recover 51.1 grams of encapsulated aluminum-zirconium salt.

EXAMPLE 9

150 grams cyclomethicone comprised mostly of octamethylcyclotetrasiloxane and decamethylcyclopentasiloxane and 28.53 grams of a silicone carboxy acid having the formula

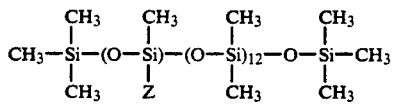

where Z is —(CH$_2$)$_{10}$COOH were combined in a 500 ml round bottom flask equipped with a paddle-blade agitator, a water cooled condenser and a 250 ml round bottom receiver. The mixture was heated to 80° C. 150 grams of aqueous aluminum-zirconium tetrachlorohydrex-gly (35% solids) was added to the silicone acid solution with agitation. The mixture was heated for approximately 2.75 hours, while distilling off the water, maintaining a temperature around 104° C. The reaction was stopped when the pot temperature reached approximately 130° C. The mixture was then vacuum filtered (while hot, ~80° C.), using a Buchner funnel, to recover the encapsulated aluminum-zirconium salt.

EXAMPLE 10

150 grams cyclomethicone comprised mostly of octamethylcyclotetrasiloxane and decamethylcyclopentasiloxane and 51.26 grams of a silicone carboxy acid having the formula

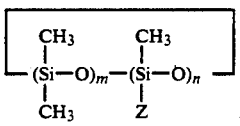

where m has the value of 2 to 5 (mostly 3 to 4), n has the value of 1 and Z is —(CH$_2$)$_{10}$COOH were combined in a 500 ml round bottom flask equipped with a paddle-blade agitator, a water cooled condenser and a 250 ml round bottom receiver. The mixture was heated to 120° C. 150 grams of aqueous aluminum-zirconium tetrachlorohydrex-gly (35% solids) was added to the silicone acid solution with agitation. The mixture was heated for approximately 2.5 hours, while distilling off the water, maintaining a temperature around 107° C. The reaction was stopped when the pot temperature reached approximately 128° C. The mixture was then vacuum filtered (while hot, ~85° C.), using a Buchner funnel, to recover the encapsulated aluminum-zirconium salt.

EXAMPLE 11

150 grams of hydroxy endblocked polydimethylsiloxane and 6.3 grams of a silicone carboxy acid having the formula

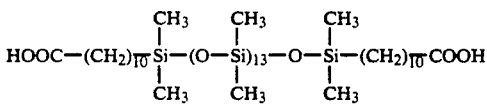

were combined in a 500 ml round bottom flask equipped with a paddle-blade agitator, a water cooled condenser and a 250 ml round bottom receiver. The mixture was heated to 80° C. 150 grams of aqueous aluminum-zirconium tetrachlorohydrex-gly (35% solids) was added to the silicone acid solution with agitation. The mixture was agitated for approximately 2 hours following the addition. The mixture was then heated for approximately 7.5 hours, while distilling off the water, maintaining a temperature around 100° C. The reaction was stopped when the pot temperature reached approximately 129° C. The mixture was then vacuum filtered using a Buchner funnel, to recover the encapsulated aluminum-zirconium salt. The encapsulated aluminum-zirconium salt was reslurried in 125 grams of a mixture comprised of cyclomethicone and hydroxy endblocked polydimethylsiloxane and refiltered. The beads appear very small and spherical when observed under an optical microscope.

What is claimed is:

1. Encapsulated aluminum salt compositions comprising
   (I) an aluminum salt selected from the group consisting of aluminum halohydrates, aluminum nitrohydrates, and mixtures thereof; contained in a shell comprising
   (II) a silicone carboxy acid, silicone carboxy acid derivative or mixture thereof selected from silicone carboxy acids or silicone carboxy acid derivatives having the formula

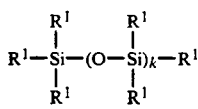

and

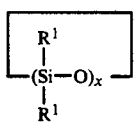

wherein each $R^1$ is independently selected from the group consisting of an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group, and a carboxy functional group having at least 2 carbon atoms, with the provision that at least one $R^1$ group is a carboxy functional group; k has the value of 1 to 1,000 and x has the value of 3 to 10.

2. A composition as claimed in claim 1 wherein the aluminum salt is aluminum chlorohydrate.

3. Encapsulated aluminum-zirconium salt compositions comprising
   (I) an aluminum-zirconium salt selected from the group consisting of aluminum-zirconium halohydrates, and mixtures thereof; contained in a shell comprising
   (II) a silicone carboxy acid, silicone carboxy acid derivative or mixture thereof selected from silicone carboxy acids or silicone carboxy acid derivatives having the formula

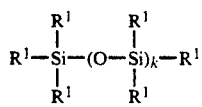

and

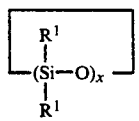

wherein each $R^1$ is independently selected from the group consisting of an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group, and a carboxy functional group having at least 2 carbon atoms, with the provision that at least one $R^1$ group is a carboxy functional group; k has the value of 1 to 1,000 and x has the value of 3 to 10.

4. A compositional as claimed in claim 3 wherein the aluminum-zirconium salt is aluminum-zirconium chlorohydrate.

5. A method for producing encapsulated aluminum salt compositions comprising
   (A) mixing together (i) an aqueous aluminum salt selected from the group consisting of aluminum halohydrates, aluminum nitrohydrates, and mixtures thereof;
(ii) a non-water miscible hydrophobic liquid selected from the group consisting of low viscosity silicone fluids, paraffin oils and mixtures thereof; and
(iii) a silicone carboxy acid, silicone carboxy acid derivative or mixture thereof selected from silicone carboxy acids or silicone carboxy acid derivatives having the formula:

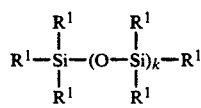

and

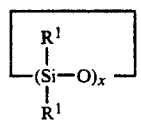

wherein each $R^1$ is independently selected from the group consisting of an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group, and a carboxy functional group having at least 2 carbon atoms, with the provision that at least one $R^1$ group is a carboxy functional group; k has the value of 1 to 1,000 and x has the value of 3 to 10;

(B) heating the mixture of (A) to remove substantially all free water; and
(C) recovering the encapsulated aluminum salt.

6. A method as claimed in claim 5 wherein the aluminum salt is aluminum chlorohydrate.

7. A method as claimed in claim 5 wherein the hydrophobic liquid is selected from low viscosity silicones.

8. A method as claimed in claim 7 wherein the hydrophobic liquid is selected from cyclic low viscosity silicones having the formula

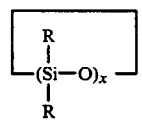

wherein each R is independently selected from the group consisting of an alkyl group containing 1 to 30 carbon atoms and an aryl group containing 6 to 10 carbon atoms and x has the value of 3 to 10.

9. A method as claimed in claim 7 wherein the hydrophobic liquid is selected from linear low viscosity silicones having the formula

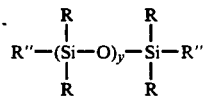

wherein each R is independently selected from the group consisting of an alkyl group containing 1 to 30 carbon atoms and an aryl group containing 6 to 10 carbon atoms; each R″ is independently selected from the group consisting of R and a hydroxyl group; and y has the value such that the viscosity of the silicone is less than 1,000 centistokes.

10. A method as claimed in claim 5 wherein the mixture is heated in step (B) to a temperature of between 100° C. and 150° C.

11. A method as claimed in claim 5 wherein the encapsulated aluminum salt is recovered through filtration means.

12. A method for producing encapsulated aluminum-zirconium salt compositions comprising (A) mixing together
  (i) an aqueous aluminum-zirconium salt selected from the group consisting of aluminum-zirconium halohydrates, and mixtures thereof;
  (ii) a non-water miscible hydrophobic liquid selected from the group consisting of low viscosity silicone fluids, paraffin oil and mixtures thereof; and
  (iii) a silicone carboxy acid, silicone carboxy acid derivative or mixture thereof selected from silicone carboxy acids or silicone carboxy acid derivatives having the formula

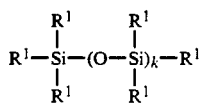

and

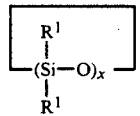

wherein each $R^1$ is independently selected from the group consisting of an alkyl group containing 1 to 30 carbon atoms, an aryl group containing 6 to 10 carbon atoms, an alkaryl group containing 7 to 20 carbon atoms, an aralkyl group containing 7 to 20 carbon atoms, a hydroxyl group, and a carboxy functional group having at least 2 carbon atoms, with the provision that at least one $R^1$ group is a carboxy functional group; k has the value of 1 to 1,000 and x has the value of 3 to 10;

(B) heating the mixture of (A) to remove substantially all free water; and (C) recovering the encapsulated aluminum-zirconium salt.

13. A method as claimed in claim 12 wherein the aluminum-zirconium salt is aluminum-zirconium chlorohydrate.

14. A method as claimed in claim 12 wherein the hydrophobic liquid is selected from low viscosity silicones.

15. A method as claimed in claim 14 wherein the hydrophobic liquid is selected from cyclic low viscosity silicones having the formula

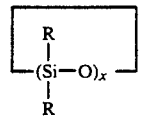

wherein each R is independently selected from an alkyl group containing 1 to 30 carbon atoms and an aryl group containing 6 to 10 carbon atoms and x has the value of 3 to 10.

16. A method as claimed in claim 14 wherein the hydrophobic liquid is selected from linear low viscosity silicones having the formula

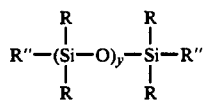

wherein each R is independently selected from the group consisting of an alkyl group containing 1 to 30 carbon atoms and an aryl group containing 6 to 10 carbon atoms; each R″ is independently selected from the group consisting of R and a hydroxyl group; and y has the value such that the viscosity of the silicone is less than 1,000 centistokes.

17. A method as claimed in claim 12 wherein the mixture is heated in step (B) to a temperature of between 100° C. and 150° C.

18. A method as claimed in claim 12 wherein the encapsulated aluminum-zirconium salt is recovered through filtration means.

19. An aerosol composition comprising
(A) 1% to 25% by weight of the encapsulated aluminum salt composition as claimed in claim 1;
(B) 50 to 90% by weight of propellant; and
(C) 5 to 15% by weight of an anhydrous carrier liquid.

20. The aerosol composition as claimed in claim 19 wherein the composition is comprised of 8 to 12 wt. % of the encapsulated aluminum salt composition.

21. A stick composition comprising
(A) 1% to 25% by weight of the encapsulated aluminum salt composition as claimed in claim 1;
(B) 20 to 65% by weight of a carrier fluid; and
(C) 5 to 30% by weight of a gellant.

22. An roll-on composition comprising
(A) 1% to 25% by weight of the encapsulated aluminum salt composition as claimed in claim 1; and
(B) 60 to 90% by weight of a carrier liquid.

23. An aerosol composition comprising
(A) 1% to 20% by weight of the encapsulated aluminum-zirconium salt composition as claimed in claim 3;
(B) 50 to 90% by weight of propellant; and
(C) 5 to 15% by weight of an anhydrous carrier liquid.

24. The aerosol composition as claimed in claim 23 wherein the composition is comprised of 8 to 12 wt. % of the encapsulated aluminum-zirconium composition.

25. A stick composition comprising
(A) 1% to 20% by weight of the encapsulated aluminum-zirconium salt composition as claimed in claim 3;
(B) 20 to 65% by weight of a carrier fluid; and
(C) 5 to 30% by weight of a gellant.

26. An roll-on composition comprising
(A) 1% to 20% by weight of the encapsulated aluminum-zirconium salt composition as claimed in claim 3; and
(B) 60 to 90% by weight of a carrier liquid.

* * * * *